United States Patent
Moua et al.

(10) Patent No.: US 9,649,152 B2
(45) Date of Patent: *May 16, 2017

(54) SURGICAL FORCEPS

(71) Applicant: COVIDIEN LP, Mansfield, MA (US)

(72) Inventors: Tony Moua, Broomfield, CO (US); David N. Heard, Boulder, CO (US); Jonathan A. Coe, Menlo Park, CA (US); John J. Kappus, Lousville, CO (US); Peter M. Mueller, Frederick, CO (US); Raymond A. Sirianne, Evergreen, CO (US); Ryan C. Artale, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/082,189

(22) Filed: Mar. 28, 2016

(65) Prior Publication Data
US 2016/0206368 A1 Jul. 21, 2016

Related U.S. Application Data

(63) Continuation of application No. 14/721,394, filed on May 26, 2015, now Pat. No. 9,358,028, which is a
(Continued)

(51) Int. Cl.
*A61B 18/14* (2006.01)
*A61B 18/12* (2006.01)
(Continued)

(52) U.S. Cl.
CPC ........ *A61B 18/1445* (2013.01); *A61B 17/295* (2013.01); *A61B 18/1206* (2013.01);
(Continued)

(58) Field of Classification Search
None
See application file for complete search history.

(56) References Cited

U.S. PATENT DOCUMENTS 2,801,633 A 8/1957 Ehrlich
5,100,420 A 3/1992 Green et al.
(Continued)

FOREIGN PATENT DOCUMENTS

AU 2011253698 A1 12/2011
CN 21299462 9/2009
(Continued)

OTHER PUBLICATIONS

U.S. Appl. No. 13/249,024, John R. Twomey.
(Continued)

*Primary Examiner* — Brian T Gedeon

(57) ABSTRACT

A forceps includes an end effector assembly including first and second jaw members. One or both of the jaw members is movable relative to the other between a spaced-apart position and an approximated position for grasping tissue therebetween. One or both of the jaw members is configured to conduct energy between the jaw members and through tissue grasped therebetween to treat tissue. An insulative tubular member is movable relative to the end effector assembly between a retracted position, wherein the insulative tubular member is positioned proximally of the end effector assembly, and an extended position, wherein the insulative tubular member is disposed about the end effector assembly. A monopolar member is configured to apply energy to tissue to treat tissue when the insulative tubular member is disposed in the extended position.

20 Claims, 9 Drawing Sheets

Related U.S. Application Data continuation of application No. 13/537,577, filed on Jun. 29, 2012, now Pat. No. 9,039,691.

(51) Int. Cl.
   *A61B 17/295* (2006.01)
   *A61B 17/00* (2006.01)
   *A61B 17/29* (2006.01)
   *A61B 18/00* (2006.01)

(52) U.S. Cl.
   CPC .......... *A61B 2017/00017* (2013.01); *A61B 2017/2901* (2013.01); *A61B 2018/0063* (2013.01); *A61B 2018/00589* (2013.01); *A61B 2018/00595* (2013.01); *A61B 2018/00601* (2013.01); *A61B 2018/00607* (2013.01); *A61B 2018/00946* (2013.01); *A61B 2018/124* (2013.01); *A61B 2018/126* (2013.01); *A61B 2018/1253* (2013.01); *A61B 2018/1273* (2013.01); *A61B 2018/1422* (2013.01); *A61B 2018/1432* (2013.01); *A61B 2018/1452* (2013.01); *A61B 2018/1467* (2013.01); *A61B 2018/1475* (2013.01); *A61B 2018/1495* (2013.01)

(56) References Cited

U.S. PATENT DOCUMENTS

| | | |
|---|---|---|
| 5,242,456 A | 9/1993 | Nash et al. |
| 5,342,359 A | 8/1994 | Rydell |
| 5,368,600 A | 11/1994 | Failla et al. |
| 5,383,471 A | 1/1995 | Funnell |
| 5,456,684 A | 10/1995 | Schmidt et al. |
| 5,707,392 A | 1/1998 | Kortenbach |
| H1745 H | 8/1998 | Paraschac |
| 6,117,158 A | 9/2000 | Measamer et al. |
| H1904 H | 10/2000 | Yates et al. |
| H2037 H | 7/2002 | Yates et al. |
| 6,733,514 B2 | 5/2004 | Miser |
| 7,103,947 B2 | 9/2006 | Sartor et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| 7,232,440 B2 | 6/2007 | Dumbauld et al. |
| D547,154 S | 7/2007 | Lee |
| 7,244,257 B2 | 7/2007 | Podhajsky et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,431,730 B2 | 10/2008 | Viola |
| D582,038 S | 12/2008 | Swoyer et al. |
| 7,594,313 B2 | 9/2009 | Prakash et al. |
| 7,641,653 B2 | 1/2010 | Dalla Betta et al. |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,896,878 B2 | 3/2011 | Johnson et al. |
| D649,249 S | 11/2011 | Guerra |
| D649,643 S | 11/2011 | Allen, IV et al. |
| D661,394 S | 6/2012 | Romero et al. |
| 8,246,618 B2 | 8/2012 | Bucciaglia et al. |
| 8,328,802 B2 | 12/2012 | Deville et al. |
| 8,920,461 B2 | 12/2014 | Unger et al. |
| 8,926,610 B2 | 1/2015 | Hafner et al. |
| 2002/0058925 A1 | 5/2002 | Kaplan et al. |
| 2008/0015566 A1 | 1/2008 | Livneh |
| 2009/0012520 A1 | 1/2009 | Hixson et al. |
| 2009/0043304 A1 | 2/2009 | Tetzlaff et al. |
| 2009/0043305 A1 | 2/2009 | Brodbeck et al. |
| 2009/0088743 A1 | 4/2009 | Masuda |
| 2009/0088750 A1 | 4/2009 | Hushka et al. |
| 2009/0182327 A1 | 7/2009 | Unger |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0009864 A1 | 1/2011 | Bucciaglia et al. |
| 2011/0071522 A1 | 3/2011 | Dumbauld et al. |
| 2011/0087218 A1 | 4/2011 | Boudreaux et al. |
| 2011/0130757 A1 | 6/2011 | Horlle et al. |
| 2011/0251606 A1 | 10/2011 | Kerr |
| 2011/0264093 A1 | 10/2011 | Schall |
| 2011/0319888 A1 | 12/2011 | Mueller et al. |
| 2012/0083786 A1 | 4/2012 | Artale et al. |
| 2012/0330351 A1 | 12/2012 | Friedman et al. |
| 2013/0165907 A1 | 6/2013 | Attar et al. |
| 2014/0276797 A1 | 9/2014 | Batchelor et al. |

FOREIGN PATENT DOCUMENTS

| | | |
|---|---|---|
| CN | 203736301 U | 7/2014 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| EP | 1530952 | 5/2005 |
| JP | 61-501068 | 9/1984 |
| JP | 10-24051 A | 1/1989 |
| JP | 11-47150 A | 6/1989 |
| JP | 6502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 3/1996 |
| JP | 08252263 A | 10/1996 |
| JP | 8-289895 A | 11/1996 |
| JP | 8-317934 A | 12/1996 |
| JP | 9-10223 | 1/1997 |
| JP | 9-122138 A | 5/1997 |
| JP | 0010000195 A | 1/1998 |

(56) References Cited

FOREIGN PATENT DOCUMENTS

| | | | |
|---|---|---|---|
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 201128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-237574 A | 9/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2006-116320 A | 5/2006 |
| JP | 2007-098136 A | 4/2007 |
| JP | 2008-246222 A | 10/2008 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 A2 | 6/2002 |
| WO | 2005/110264 A2 | 11/2005 |

OTHER PUBLICATIONS

U.S. Appl. No. 13/251,380, Duane E. Kerr.
U.S. Appl. No. 13/277,373, Glenn A. Homer.
U.S. Appl. No. 13/277,926, David M. Garrison.
U.S. Appl. No. 13/277,962, David M. Garrison.
U.S. Appl. No. 13/293,754, Jeffrey M. Roy.
U.S. Appl. No. 13/306,523, David M. Garrison.
U.S. Appl. No. 13/306,553, Duane E. Kerr.
U.S. Appl. No. 13/308,104, John R. Twomey.
U.S. Appl. No. 13/312,172, Robert J. Behnke, II.
U.S. Appl. No. 13/324,863, William H. Nau, Jr.
U.S. Appl. No. 13/344,729, James D. Allen, IV.
U.S. Appl. No. 13/355,829, John R. Twomey.
U.S. Appl. No. 13/357,979, David M. Garrison.
U.S. Appl. No. 13/358,136, James D. Allen, IV.
U.S. Appl. No. 13/360,925, James H. Orszulak.
U.S. Appl. No. 13/400,290, Eric R. Larson.
U.S. Appl. No. 13/404,435, Kim V. Brandt.
U.S. Appl. No. 13/404,476, Kim V. Brandt.
U.S. Appl. No. 13/412,879, David M. Garrison.
U.S. Appl. No. 13/412,897, Joanna Ackley.
U.S. Appl. No. 13/421,373, John R. Twomey.
U.S. Appl. No. 13/430,325, William H. Nau, Jr.
U.S. Appl. No. 13/433,924, Keir Hart.
U.S. Appl. No. 13/448,577, David M. Garrison.
U.S. Appl. No. 13/460,455, Luke Waaler.
U.S. Appl. No. 13/461,335, James D. Allen, IV.
U.S. Appl. No. 13/461,378, James D. Allen, IV.
U.S. Appl. No. 13/461,397, James R. Unger.
U.S. Appl. No. 13/461,410, James R. Twomey.
U.S. Appl. No. 13/464,569, Duane E. Kerr.
U.S. Appl. No. 13/466,274, Stephen M. Kendrick.
U.S. Appl. No. 13/467,767, Duane E. Kerr.
U.S. Appl. No. 13/470,543, Sean T. Dycus.
U.S. Appl. No. 13/470,775, James D. Allen, IV.
U.S. Appl. No. 13/470,797, John J. Kappus.
U.S. Appl. No. 13/482,589, Eric R. Larson.
U.S. Appl. No. 13/483,733, Dennis W. Butcher.
U.S. Appl. No. 13/488,093, Kristin D. Johnson.
U.S. Appl. No. 13/491,853, Jessica E. Olson.
U.S. Appl. No. 13/537,517, David N. Heard.
U.S. Appl. No. 13/537,577, Tony Moua.
U.S. Appl. No. 13/550,322, John J. Kappus.
U.S. Appl. No. 13/571,055, Paul Guerra.
U.S. Appl. No. 13/571,821, Joseph D. Bucciaglia.
U.S. Appl. No. 13/584,194, Sean T. Dycus.
European Search Report EP13174297 dated Nov. 7, 2013.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Michael Choti, "Abdominoperineal Resection with the LigaSure Vessel Sealing System and LigaSure Atlas 20 cm Open Instrument" Innovations That Work, .quadrature.Jun. 2003.
Chung et al., "Clinical Experience of Sutureless Closed Hemorrhoidectomy with LigaSure" Diseases of the Colon & Rectum vol. 46, No. 1 Jan. 2003. cited by applicant.
Tinkcler L.F., "Combined Diathermy and Suction Forceps", Feb. 6, 1967 (Feb. 6, 1965), British Medical Journal Feb. 3, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small,

(56) References Cited

OTHER PUBLICATIONS

Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. cited by applicant.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).

Muller et al., "Extended Left Hemicoletomy Using the LigaSure Vessel Sealing System" Innovations That Work,. quadrature.Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work,.quadrature. Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for be Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.

(56) References Cited

OTHER PUBLICATIONS

Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson. "Use of the LigaSure Vessel Sealing System in Bloodless Hemorrhoidectomy" That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Perl-Hilar Vessels in Laparoscopic Nephrectomy" Sales Product Literature.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Chinese Office Action from corresponding Chinese Patent Appln. No. 201310237636.3 dated Mar. 2, 2015.
Chinese Office Action issued in corresponding application No. 201310237630.6 on Sep. 1, 2015.
Canadian Office Action issued in corresponding application No. 2,815,875 on Jul. 23, 2015.
Japanese office action issued in corresponding application No. 2014-227674 on Sep. 25, 2015.
Chinese Office Action issued in corresponding application No. 201310237636.3 on Oct. 10, 2015.
Canadian office action issued in corresponding application No. 2815875 on May 6, 2016.
US. Appl. No. 08/926,869, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/050,182, filed Mar. 17, 2011, Glenn A. Horner.
U.S. Appl. No. 13/072,945, Patrick L. Dumbauld.
U.S. Appl. No. 13/080,383, David M. Garrison.
U.S. Appl. No. 13/085,144, filed Apr. 12, 2011, Keir Hart.
U.S. Appl. No. 13/091,331, Jeffrey R. Townsend.
U.S. Appl. No. 13/102,573, John R. Twomey.
U.S. Appl. No. 13/102,604, Paul E. Ourada.
U.S. Appl. No. 13/108,093, Boris Chernov.
U.S. Appl. No. 13/108,129, Boris Chernov.
U.S. Appl. No. 13/108,152, Boris Chernov.
U.S. Appl. No. 13/108,177, Boris Chernov.
U.S. Appl. No. 13/108,196, Boris Chernov.
U.S. Appl. No. 13/108,441, Boris Chernov.
U.S. Appl. No. 13/108,468, Boris Chernov.
U.S. Appl. No. 13/111,642, John R. Twomey.
U.S. Appl. No. 13/111,678, Nikolay Kharin.
U.S. Appl. No. 13/113,231, David M. Garrison.
U.S. Appl. No. 13/157,047, John R. Twomey.
U.S. Appl. No. 13/162,814, Barbara R. Tyrrell.
U.S. Appl. No. 13/166,477, Daniel A. Joseph.
U.S. Appl. No. 13/166,497, Daniel A. Joseph.
U.S. Appl. No. 13/179,919, Russell D. Hempstead.
U.S. Appl. No. 13/179,960, Boris Chernov.
U.S. Appl. No. 13/179,975, Grant T. Sims.
U.S. Appl. No. 13/180,018, Chase Collings.
U.S. Appl. No. 13/183,856, John R. Twomey.
U.S. Appl. No. 13/185,593, James D. Allen, IV.
U.S. Appl. No. 13/204,841, Edward J. Chojin.
U.S. Appl. No. 13/205,999, Jeffrey R. Unger.
U.S. Appl. No. 13/212,297, Allan J. Evans.
U.S. Appl. No. 13/212,308, Allan J. Evans.
U.S. Appl. No. 13/212,329, Allan J. Evans.
U.S. Appl. No. 13/212,343, Duane E. Kerr.
U.S. Appl. No. 13/223,521, John R. Twomey.
U.S. Appl. No. 13/227,220, James D. Allen, IV.
U.S. Appl. No. 13/228,742, Duane E. Kerr.
U.S. Appl. No. 13/231,643, Keir Hart.
U.S. Appl. No. 13/234,357, James D. Allen, IV.
U.S. Appl. No. 13/236,168, James D. Allen, IV.
U.S. Appl. No. 13/236,271, Monte S. Fry.
U.S. Appl. No. 13/243,628, William Ross Whitney.
U.S. Appl. No. 13/247,778, John R. Twomey.
U.S. Appl. No. 13/247,795, John R. Twomey.
U.S. Appl. No. 13/248,976, James D. Allen, IV.
U.S. Appl. No. 13/249,013, Jeffrey R. Unger.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 11 006233.8 dated Feb. 2, 2012.

(56) References Cited

OTHER PUBLICATIONS

Int'l Search Report EP 11 007972.0 dated Dec. 28, 2011.
Int'l Search Report EP 11 151509.4 dated Jun. 6, 2011.
Canadian office action issued in corresponding application No. 2816192 on Aug. 26, 2016.
Canadian office action issued in corresponding application No. 2815875 on Mar. 17, 2017.

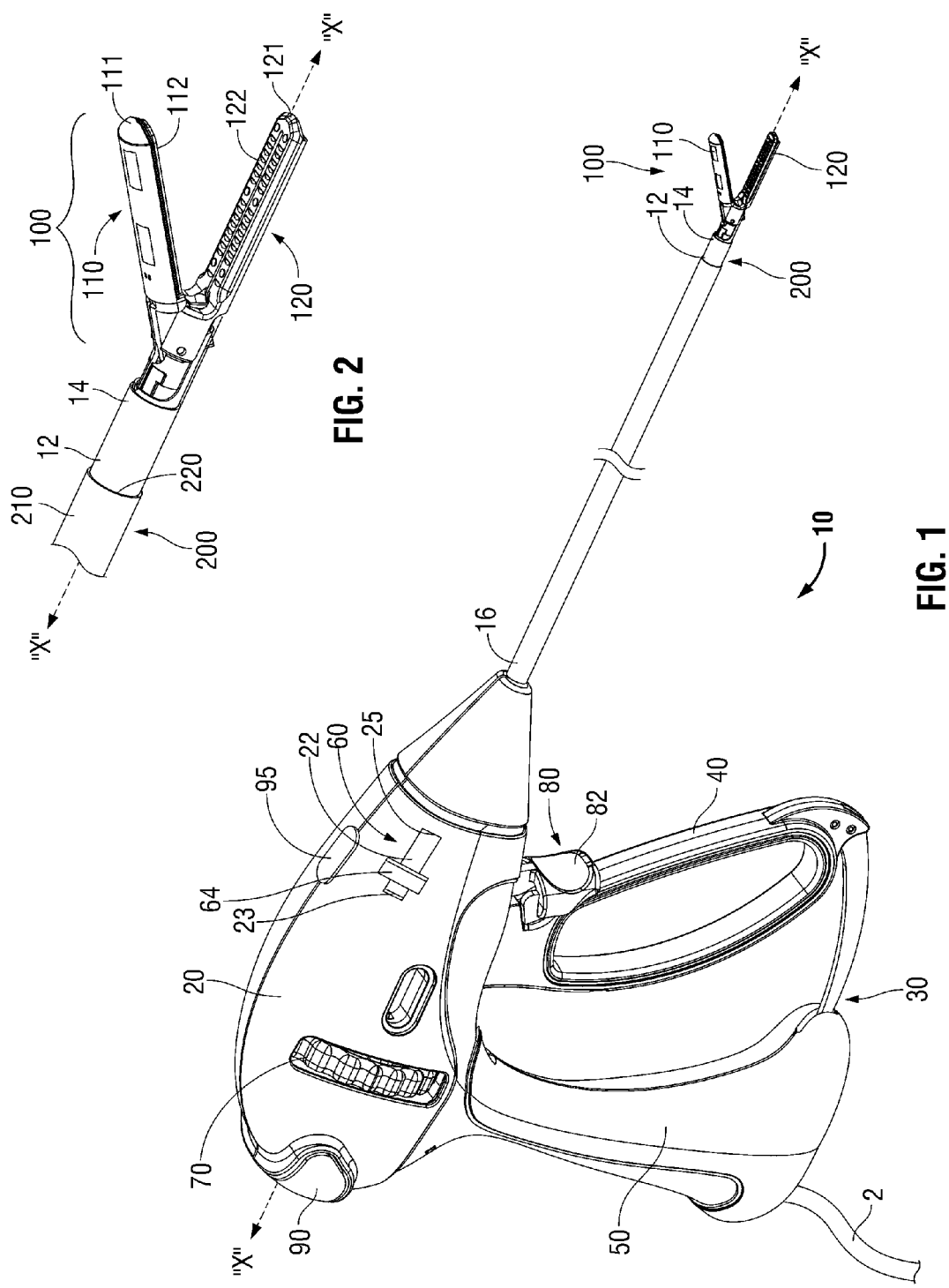

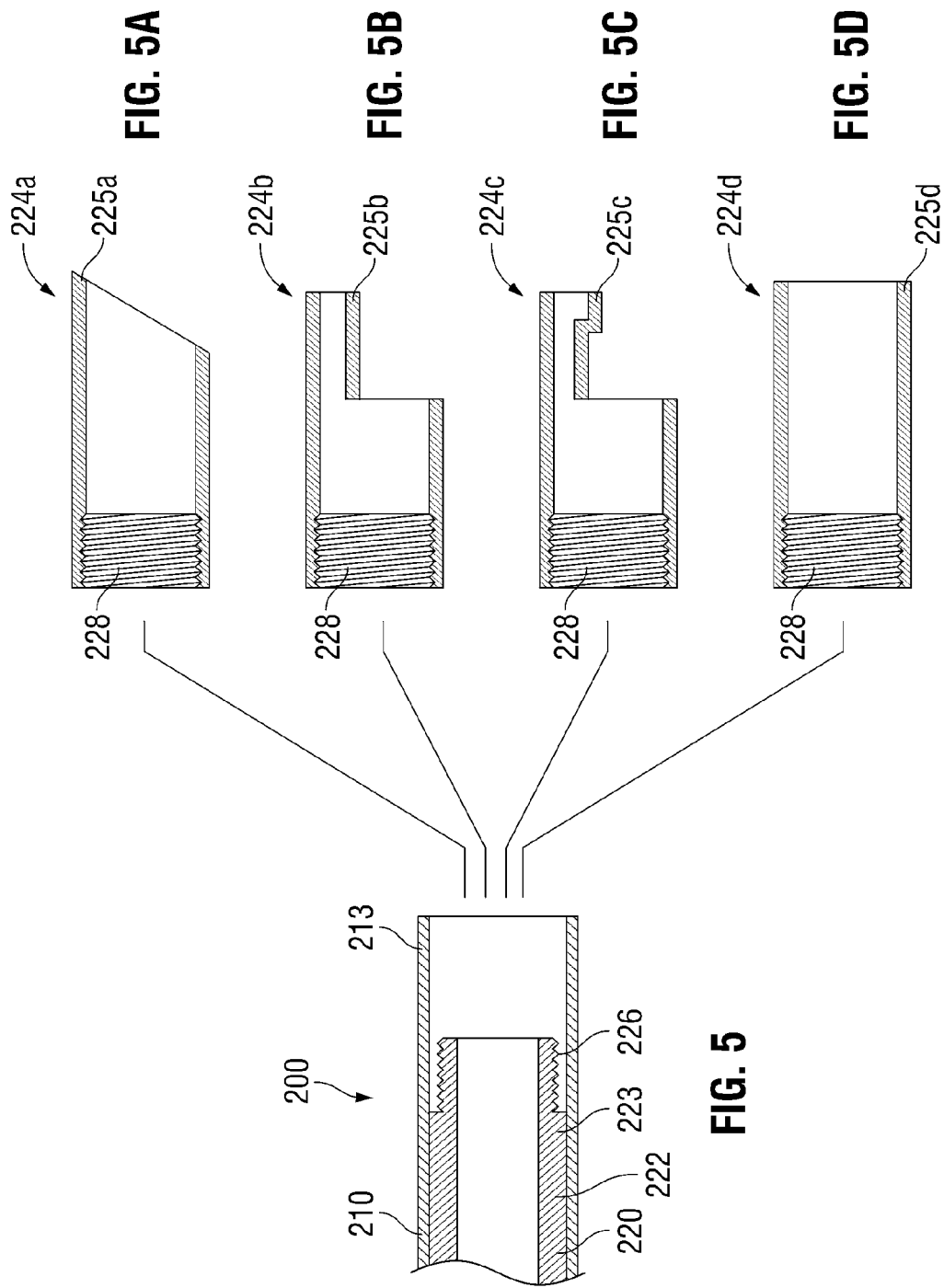

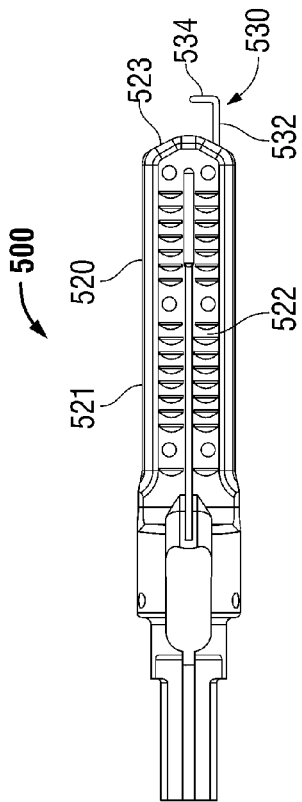
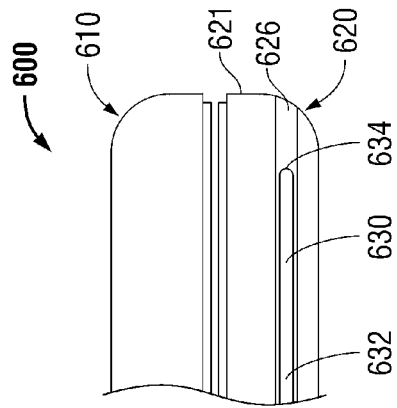
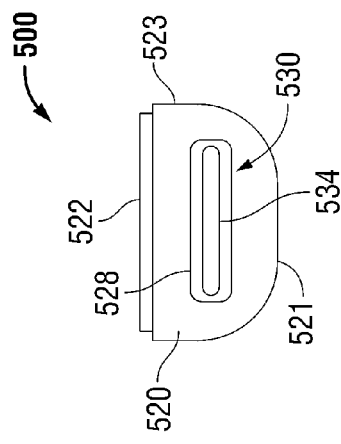
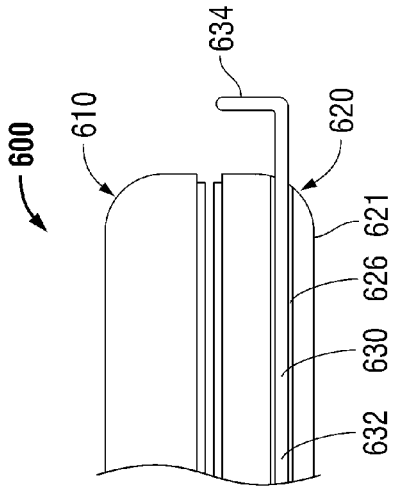

SURGICAL FORCEPS

CROSS-REFERENCE TO RELATED APPLICATIONS

This application is a continuation application of U.S. patent application Ser. No. 14/721,394, filed on May 26, 2015, which is a continuation application of U.S. patent application Ser. No. 13/537,577, filed on Jun. 29, 2012, now U.S. Pat. No. 9,039,691, the entire contents of each of which is hereby incorporated herein by reference.

BACKGROUND

Technical Field

The present disclosure relates to surgical instruments and, more particularly, to a bipolar surgical forceps including an extendable monopolar element.

Background of Related Art

Bipolar electrosurgical forceps typically include two generally opposing electrodes charged to different electric potentials to selectively apply energy to tissue. Bipolar electrosurgical forceps utilize both mechanical clamping action and electrical energy to effect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many forceps have been designed which incorporate a knife or blade member that effectively severs the tissue after forming a tissue seal.

Monopolar surgical instruments, on the other hand, include an active electrode, and are used in conjunction with a remote return electrode, e.g., a return pad, to apply energy to tissue. Monopolar instruments have the ability to rapidly move through tissue and dissect through narrow tissue planes.

In some surgical procedures, it may be beneficial to use both bipolar and monopolar instrumentation, e.g., procedures where it is necessary to dissect through one or more layers of tissue in order to reach underlying tissue(s) to be sealed. Further, it may be beneficial, particularly with respect to endoscopic surgical procedures, to provide a singe instrument incorporating both bipolar and monopolar features, thereby obviating the need to alternatingly remove and insert the bipolar and monopolar instruments in favor of one another.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any of the other aspects described herein.

In accordance with aspects of the present disclosure, a forceps is provided including an end effector assembly having first and second jaw members. One or both of the jaw members is movable relative to the other between a spaced-apart position and an approximated position for grasping tissue therebetween. One or both of the jaw members is configured to conduct energy between the jaw members and through tissue grasped therebetween to treat tissue. The forceps also includes an insulative tubular member movable relative to the end effector assembly between a retracted position, wherein the insulative tubular member is positioned proximally of the end effector assembly, and an extended position, wherein the insulative tubular member is disposed about the end effector assembly. The forceps further includes a monopolar member configured to apply energy to tissue to treat tissue when the insulative tubular member is disposed in the extended position.

In one aspect, the monopolar member includes an inner tubular member disposed within and engaged to the insulative tubular member. A portion of the inner tubular member extends distally from the insulative tubular member such that, in the extended position of the insulative tubular member, the portion of the inner tubular member extends distally from the end effector assembly for applying energy to tissue to treat tissue.

In another aspect, the portion of the inner tubular member that extends distally from the insulative tubular member is further configured to facilitate mechanical dissection of tissue.

In another aspect, the portion of the inner tubular member that extends distally from the insulative tubular member includes one of a beveled distal end, an annular distal end, a blade extending distally therefrom, and a hook extending distally therefrom.

In still another aspect, the inner tubular member includes a releasably engagable distal tip. The releasably engagable distal tip extends distally from the insulative tubular member. Further, the releasably engagable distal tip may be selected from a plurality of distal tips including one or more of a first distal tip including a beveled distal end, a second distal tip including a blade extending distally therefrom, a third distal tip including a hook extending distally thereform, and a fourth distal tip including an annular distal end.

In yet another aspect, the forceps further includes a shaft coupled to the end effector assembly at a distal end of the shaft. In such aspects, the insulative tubular member may be disposed about the shaft and may be slidable relative to the shaft between the retracted and extended positions.

In still yet another aspect, the forceps further includes a slide assembly including a slide knob. The slide knob is coupled to the insulative tubular member and selectively movable between a first position and a second position for moving the insulative tubular member between the retracted and extended positions.

In another aspect, the forceps further includes a first activation switch for selectively supplying energy to the jaw member(s) and a second activation switch for selectively supplying energy to the monopolar member. Further, the first activation switch and/or the second activation switch may be inhibited from being activated when the insulative tubular member is disposed in the extended and retracted positions, respectively.

In yet another aspect, one or both of the jaw members includes a distal tip portion. The distal tip portion of the jaw member(s) defines the monopolar member for applying energy to tissue to treat tissue when the insulative tubular member is disposed in the extended position. The distal tip portion of the jaw member(s) may further be configured to facilitate mechanical dissection of tissue. Additionally, the insulative tubular member may define a cut-out. In such a configuration, the distal tip portion of the jaw member(s) may be configured to extend through the cut-out when the insulative tubular member is disposed in the extended position.

Another forceps provided in accordance with aspects of the present disclosure includes an end effector assembly including first and second jaw members. One or both of the jaw members is movable relative to the other between a spaced-apart position and an approximated position for grasping tissue therebetween. One or both of the jaw members is configured to conduct energy between the jaw members and through tissue grasped therebetween to treat tissue. The forceps further includes a monopolar assembly. The monopolar assembly includes an insulative tubular member and an electrically-conductive distal member configured to apply energy to tissue to treat tissue. The electrically-conductive distal member is engaged to and extends distally from the insulative tubular member. The monopolar assembly is movable relative to the end effector assembly between a retracted position, wherein the monopolar assembly is positioned proximally of the end effector assembly, and an extended position, wherein the insulative tubular member substantially surrounds the end effector assembly and the electrically-conductive distal member extends distally from the end effector assembly.

In one aspect, the electrically-conductive distal member includes a releasably engagable distal tip, the releasably engagable distal tip extending distally from the insulative tubular member. The releasably engagable distal tip may be selected from a plurality of distal tips including a first distal tip including a beveled distal end, a second distal tip including a blade extending distally therefrom, a third distal tip including a hook extending distally therefrom, and a fourth distal tip including an annular distal end.

In another aspect, the forceps further includes a slide assembly having a slide knob. The slide knob is coupled to the monopolar assembly and is selectively movable between a first position and a second position for moving the monopolar assembly between the retracted and extended positions.

A method of treating tissue is also provided in accordance with aspects of the present disclosure. The method includes grasping tissue between first and second jaw members, applying energy between the first and second jaw members and to tissue grasped therebetween to treat tissue, advancing a monopolar assembly including an insulative tubular member and an electrically-conductive distal member about the first and second jaw members such that the insulative tubular member substantially surrounds the first and second jaw members and the electrically-conductive distal member extends distally from the first and second jaw members, and applying energy from the electrically-conductive distal member to tissue to treat tissue.

In one aspect, the step of applying energy between the jaw members further includes sealing tissue grasped between the jaw members and the step of applying energy from the electrically-conductive distal member further includes electrically dissecting tissue.

In another aspect, the electrically-conductive distal member includes a releasably engagable distal tip. In such aspects, the method further includes selecting the distal tip from a plurality of distal tips including a first distal tip including a beveled distal end, a second distal tip including a blade extending distally therefrom, a third distal tip including a hook extending distally therefrom, and a fourth distal tip including an annular distal end, and engaging the selected distal tip to the electrically-conductive distal member.

BRIEF DESCRIPTION OF THE DRAWINGS

Various aspects of the present disclosure are described herein with reference to the drawings wherein like reference numerals identify similar or identical elements:

FIG. 1 is a front, perspective view of an endoscopic surgical forceps configured for use in accordance with the present disclosure;

FIG. 2 is an enlarged, perspective view of an end effector assembly of the forceps of FIG. 1;

FIG. 5 is a longitudinal, cross-sectional view of a distal end of the monopolar assembly of FIG. 4D;

FIGS. 5A-5D are longitudinal, cross-sectional views of various distal tips releasably engagable with the monopolar assembly of FIG. 4D;

FIG. 7A is a top view of a jaw member of another end effector assembly configured for use with the forceps of FIG. 1 with a monopolar assembly disposed in an extended position;

FIG. 7B is an end view of the jaw member of FIG. 7A with the monopolar assembly disposed in a retracted position;

FIG. 8A is a longitudinal, cross-sectional view of another end effector assembly configured for use with the forceps of FIG. 1 with a monopolar assembly disposed in a retracted position;

FIG. 8B is a longitudinal, cross-sectional view of the end effector assembly of FIG. 8A with the monopolar assembly disposed in an extended position;

DETAILED DESCRIPTION

Figure 3:
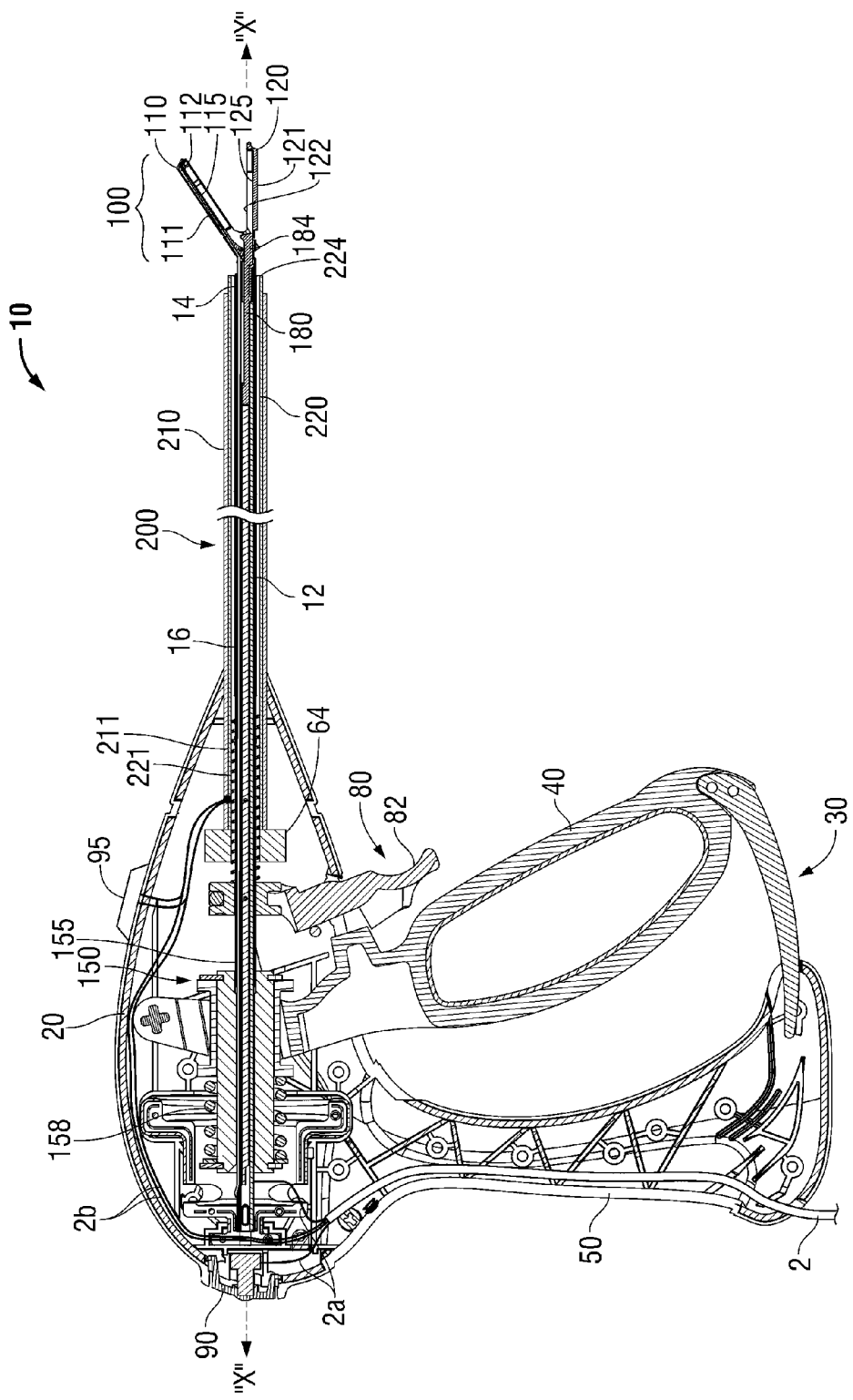
FIG. 3 is a longitudinal, cross-sectional view of the forceps of FIG. 1.

Referring now to FIGS. 1-3, a forceps including features for operating in both a bipolar mode, e.g., for grasping, treating, and/or dissecting tissue, and a monopolar mode, e.g., for treating and/or dissecting tissue, is shown generally identified by reference numeral 10. Although shown as an endoscopic forceps 10, it is contemplated that forceps 10 also be configured for use in connection with traditional open surgical procedures. Obviously, different electrical and mechanical connections and considerations apply to each particular configuration; however, the novel aspects with respect to forceps 10 and its operating characteristics remain generally consistent with respect to both the open and endoscopic configurations.

Continuing with reference to FIGS. 1-3, forceps 10 defines a longitudinal axis "X-X" and includes a housing 20, a handle assembly 30, a slide assembly 60, a rotating assembly 70, a trigger assembly 80, an end effector assembly 100, and a monopolar assembly 200. Forceps 10 further includes a shaft 12 having a distal end 14 configured to mechanically engage end effector assembly 100 and a proximal end 16 that mechanically engages housing 20. Forceps 10 also includes electrosurgical cable 2 that connects forceps 10 to a generator (not shown) or other suitable power source, although forceps 10 may alternatively be configured as a battery powered instrument. Cable 2 includes wires 2a extending therethrough that have sufficient length to extend through shaft 12 in order to provide electrical energy to at least one of the tissue sealing plates 112, 122 of jaw members 110, 120, respectively, of end effector assembly 100, e.g., upon activation of first activation switch 90. Wires 2b of cable 2, on the other hand, extend through housing 20 in order to provide electrical energy to monopolar assembly 200, e.g., upon activation of second activation switch 95, as will be described in greater detail hereinbelow.

With continued reference to FIGS. 1-3, handle assembly 30 includes fixed handle 50 and a movable handle 40. Fixed handle 50 is integrally associated with housing 20 and movable handle 40 is moveable relative to fixed handle 50. Rotating assembly 70 is rotatable in either direction about longitudinal axis "X-X" to rotate end effector 100 about longitudinal axis "X-X." Housing 20 houses the internal working components of forceps 10.

Referring still to FIGS. 1-3, end effector assembly 100 is shown attached at a distal end 14 of shaft 12 and includes a pair of opposing jaw members 110 and 120. Each of the jaw members 110 and 120 includes an electrically-insulative outer jaw housing 111, 121 and an electrically-conductive tissue sealing surface defined by an electrically-conductive plate 112, 122 disposed atop respective jaw housings 111, 121, although other configurations are contemplated, e.g., jaw members 110, 120 may be completely formed from an electrically-conductive material. Tissue sealing plates 112, 122 of jaw members 110, 120, respectively, are adapted to connect to a source of energy (not explicitly shown), e.g., via wires 2a, for conducting energy therebetween and through tissue grasped between jaw members 110, 120 to treat, e.g., seal, tissue. More specifically, end effector assembly 100 defines a bipolar configuration wherein tissue sealing plate 112 is charged to a first electrical potential and tissue sealing plate 122 is charged to a second, different electrical potential such that an electrical potential gradient is created for conducting energy between tissue sealing plates 112, 122 and through tissue grasped therebetween for treating e.g., sealing, tissue. First activation switch 90 is coupled to wires 2a, thus allowing the user to selectively apply energy to sealing plates 112, 122 of end effector assembly 100.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife assembly 180 is disposed within shaft 12 and a knife channel 115, 125 is defined within one or both jaw members 110, 120 to permit reciprocation of a knife 184 therethrough, e.g., via actuation of a trigger 82 of trigger assembly 80.

Continuing with reference to FIGS. 1-3, movable handle 40 of handle assembly 30 is ultimately connected to a drive assembly 150 that, together, mechanically cooperate to impart movement of jaw members 110 and 120 between a spaced-apart position (FIG. 4A) and an approximated position (FIG. 4B) to grasp tissue between tissue sealing plates 112 and 122 of jaw members 110, 120, respectively. More specifically, the drive assembly 150 includes a drive sleeve 155 (FIG. 3) that is operably coupled to jaw member 110 (and/or jaw member 120) such that longitudinally translation of drive sleeve 155 through shaft 12 and relative to end effector assembly 100 pivots jaw member 110 relative to jaw member 120 between the spaced-apart and approximated positions for grasping tissue therebetween. As shown in FIG. 1, movable handle 40 is initially spaced-apart from fixed handle 50 and, correspondingly, jaw members 110, 120 are disposed in the spaced-apart position. Movable handle 40 is movable from this initial position to a depressed position for translating drive sleeve 155 proximally through shaft 12 and relative to end effector assembly 100 to move jaw members 110, 120 to the approximated position for grasping tissue therebetween (see FIG. 4B). Upon release (or return) of movable handle 40, drive sleeve 155 is translated distally under the bias of biasing member 158 to return jaw members 110, 120 to the spaced-apart position.

Referring now to FIGS. 1-4D, monopolar assembly 200 of forceps 10 is shown generally including an electrically-insulative outer tubular member 210 and an electrically-conductive inner tubular member 220 that functions as the active electrode of monopolar assembly 200. Outer tubular member 210 is disposed about and fixedly engaged to inner tubular member 220 such that outer tubular member 210 and inner tubular member 220 move in concert with one another, although outer and inner tubular members 210, 220, respectively, may alternatively be movable relative to one another. Further, a second electrically-insulative member (not explicitly shown), similar to outer tubular member 210, may be positioned within electrically-conductive inner tubular member 220 such that electrically-conductive inner tubular member 220 is sandwiched between a pair of insulating tubular members, although other configurations are also contemplated.

Monopolar assembly 200 is disposed about shaft 12 with proximal ends 211, 221 of outer and inner tubular members 210, 220, respectively, extending into housing 20. Proximal end 211 of outer tubular member 210 (and/or proximal end 221 of inner tubular member 220), which extends into housing 20, is coupled within housing 20 to a slide assembly 60. Slide assembly 60 includes a slide knob 64 that extends from a slot 22 defined within housing 20 and is selectively translatable along slot 22 to translate monopolar assembly 200 relative to shaft 12 and end effector assembly 100 between a retracted position (FIGS. 4A-4C) and an extended position (FIG. 4D), as will be described in greater detail below. Alternatively, shaft 12 may be coupled to slide assembly 60 and monopolar assembly 200 may be fixedly engaged to housing 20 such that, upon translation of slide knob 64 of slide assembly 60 along slot 22, shaft 12 and end effector assembly 100 are translated relative to monopolar assembly 200 between the retracted position (FIGS. 4A-4C) and the extended position (FIG. 4D). Wires 2b of cable 2 are coupled to proximal end 221 of inner tubular member 220 to provide energy to inner tubular member 220. Second activation switch 95, disposed on housing 20, is coupled to wires 2b to allow the user to selectively control the application of energy to inner tubular member 220.

Inner tubular member 220 includes a body portion 222 and a distal tip 224. At least a portion of a distal tip 224 of inner tubular member 220 extends distally beyond distal end 213 of outer tubular member 210 of monopolar assembly 200 such that electrically-conductive distal tip 224 is at least partially exposed. Thus, in the extended position (FIG. 4D), as will be described in greater detail below, the exposed portion of electrically-conductive distal tip 224 of inner tubular member 220 extends distally beyond end effector assembly 100 to facilitate treating, e.g., mechanically, electrically, or electromechanically dissecting, tissue. For treating tissue with monopolar assembly 200, energy is applied from wires 2b, e.g., upon activation of second activation switch 95, and is conducted along inner tubular member 220 to distal tip 224 thereof for application to tissue. A return pad (not shown) is remotely placed to receive energy conducted from the monopolar electrode, e.g., inner tubular member 220 and, more specifically, distal tip 224 thereof, through tissue. Distal tip 224, as will be described in greater detail below, may be releasably engagable with body 222 of inner tubular member 220 such that monopolar assembly 200 may assume various different configurations, depending on a particular purpose.

Monopolar assembly 200 may be biased towards the retracted position and/or may include a locking assembly (not shown) for selectively locking monopolar assembly 200 in the retracted and/or the extended position. Further, internal circuitry (not explicitly shown) coupled to first and second activation switches 90, 95, respectively, and wires 2a, 2b may be provided for inhibiting energization of tissue sealing plates 112, 122 when monopolar assembly 200 is disposed in the extended position and/or for inhibiting energization of distal tip 224 of inner tubular member 220 when monopolar assembly 200 is disposed in the retracted position. Alternatively or additionally, mechanical mechanisms (not explicitly shown) for inhibiting activation of activation switches 90, 95 may also be provided for similar purposes. For example, the proximal end of monopolar assembly 200 may be configured to interfere with activation switch 95 when in the retracted position, thereby inhibiting activation of activation switch 95 when monopolar assembly 200 is disposed in the retracted position. Such features may similarly apply to any of the other embodiments described herein.

Figure 4A:
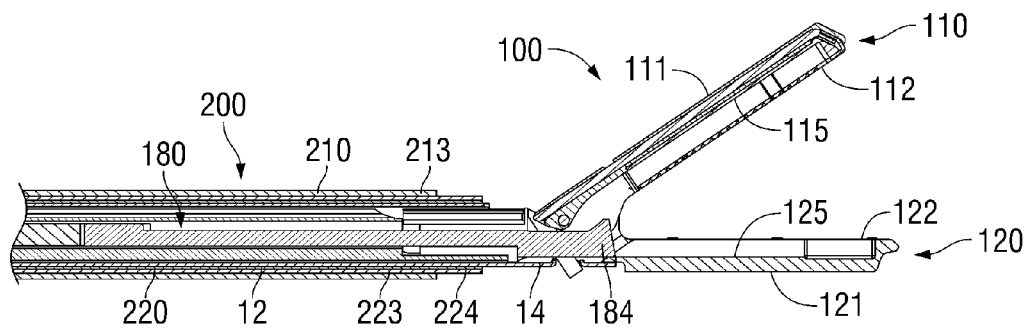
FIG. 4A is a longitudinal, cross-sectional view of the end effector assembly of FIG. 2 with jaw members of the end effector assembly disposed in a spaced-apart position.
Figure 4B:
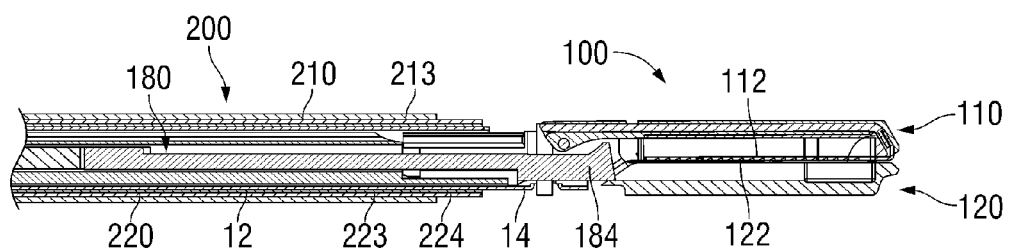
FIG. 4B is a longitudinal, cross-sectional view of the end effector assembly of FIG. 2 with the jaw members disposed in an approximated position.
Figure 4C:
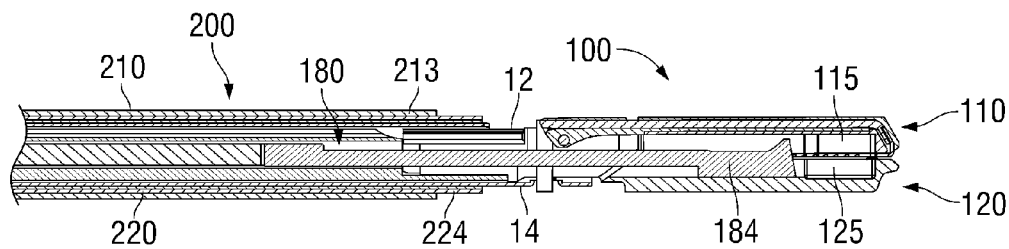
FIG. 4C is a longitudinal, cross-sectional view of the end effector assembly of FIG. 2 with the jaw members disposed in the approximated position and a knife assembly disposed in a deployed position.
Figure 4D:
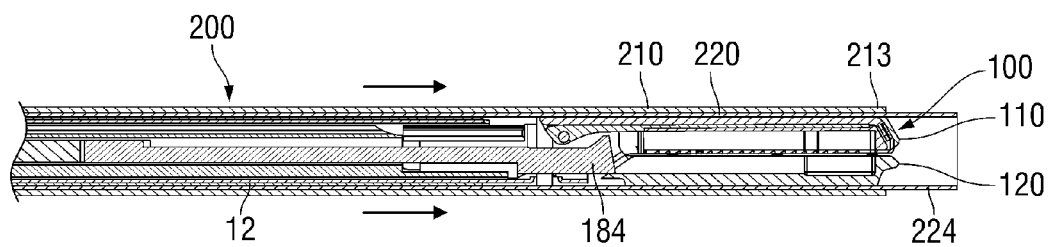
FIG. 4D is a longitudinal, cross-sectional view of the end effector assembly of FIG. 2 with a monopolar assembly disposed in an extended position.

Turning now to FIGS. 4A-4D, in conjunction with FIG. 1, the use and operation of forceps 10 in both the bipolar mode, e.g., for grasping, treating and/or cutting tissue, and the monopolar mode, e.g., for electrical/electromechanical tissue treatment, is described. Initially, with respect to the bipolar mode, as shown in FIG. 4A, jaw members 110, 120 are disposed in the spaced-apart position. In the bipolar mode, monopolar assembly 200 remains disposed in the retracted position, as shown in FIGS. 4A-4C, wherein distal tip 224 of inner tubular member 220 is positioned proximally of jaw members 110, 120. With jaw members 110, 120 disposed in the spaced-apart position, end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween, as shown in FIG. 4B. More specifically, upon actuation of movable handle 40, drive sleeve 155 (FIG. 3) is translated proximally through shaft 12, pulling jaw member 110 to pivot relative to jaw member 120 from the spaced-apart position to the approximated position. In this approximated position, energy may be supplied, e.g., via activation of switch 90, to tissue-sealing plate 112 of jaw member 110 and/or tissue-sealing plate 122 of jaw member 120 and conducted through tissue to treat tissue, e.g., to effect a tissue seal or otherwise treat tissue.

The disposition of monopolar assembly 200 in the retracted position, e.g., where distal tip 224 of inner tubular member 220 is proximally-spaced from end effector assembly 100, as well as the positioning of insulative outer tubular member 210 about inner tubular member 220, helps inhibit capacitive coupling between tissue sealing plates 112, 122 and distal tip 224 of monopolar assembly 200, e.g., helps inhibit distal tip 224 from being heated or energized, as energy is supplied to tissue sealing plate 112 and/or tissue sealing plate 122 for tissue sealing (or otherwise treating tissue). Maintaining distal tip 224 in an un-energized state while not in use helps protect tissue surrounding forceps 10.

As shown in FIG. 4C, in conjunction with FIG. 1, once tissue treatment is complete (or to cut untreated tissue), knife 184 of knife assembly 180 may be deployed from within shaft 12 to between jaw members 110, 120, e.g., via actuation of trigger 82 of trigger assembly 80, to cut tissue grasped therebetween. More specifically, upon actuation of trigger 82, knife 184 is advanced distally from shaft 12 to extend at least partially through knife channels 115, 125 of jaw members 110, 120, respectively, to cut tissue grasped between jaw members 110, 120. Thereafter, knife 184 may be returned to within shaft 12 and jaw members 110, 120 may be moved back to the spaced-apart position (FIG. 4A) to release the treated and/or divided tissue.

With reference to FIGS. 4B and 4D, in conjunction with FIG. 1, with respect to the monopolar mode, movable handle 40 is first depressed relative to fixed handle 50 to pivot jaw member 110 relative to jaw member 120 from the spaced-apart position to the approximated position. With jaw members 110, 120 disposed in the approximated position, monopolar assembly 200 may be translated from the retracted position (FIG. 4B) to the extended position (FIG. 4D). More specifically, in order to translate monopolar assembly 200 from the retracted position (FIG. 4B) to the extended position (FIG. 4D), slide knob 64 of slide assembly 60 is translated distally along slot 22 defined within housing 20 from proximal end 23 of slot 22 to distal end 25 thereof such that outer and inner tubular members 210, 220, respectively, are translated distally over shaft 12 and, ultimately, over jaw members 110, 120, respectively, until distal tip 224 of inner tubular member 220 extends distally from end effector assembly 100. In the extended position, outer tubular member 210 of monopolar assembly 200 is completely disposed over jaw members 110, 120, and a portion thereof may extend distally beyond jaw members 110, 120. In embodiments where outer and inner tubular members 210, 220 are independently movable relative to one another, multiple slide knobs 64 may be provided for moving each of outer and inner tubular members 210, 220 between the retracted and extended positions independently of one another. Other deployment mechanisms are also contemplated.

With monopolar assembly 200 disposed in the extended position, as shown in FIG. 4D, second activation switch 95 may be actuated to supply energy to inner tubular member 220 such that energy is conducted along inner tubular member 220 to distal tip 224 thereof, and from distal tip 224 to tissue to treat, e.g., dissect, tissue. As mentioned above, energy is returned via a remotely positioned return pad (not explicitly shown). During application of energy to distal tip 224, forceps 10 may be moved relative to tissue, e.g., longitudinally along longitudinal axis "X-X" and/or radially therefrom, to facilitate electromechanical treatment of tissue. Alternatively or additionally, forceps 10 may be moved relative to tissue to facilitate mechanically dissecting tissue, e.g., scoring tissue planes, with distal tip 224 in the absence of energy being applied to distal tip 224.

During application of energy to distal tip 224, outer tubular member 210 electrically insulates body portion 222 of inner tubular member 220 from surrounding tissue to help protect the surrounding tissue. Further, with jaw members 110, 120 disposed in the approximated position, insulative jaw housings 111, 121 insulate the respective tissue sealing plates 112, 122 from inner tubular member 220 to help inhibit capacitive coupling therebetween. As mentioned above, a second electrically-insulative member (not explicitly shown) may be positioned within electrically-conductive inner tubular member 220 to facilitate the isolation of tissue sealing plates 112, 122 from distal tip 224 when monopolar assembly 220 is disposed in the retracted position. In either configuration, damage to surrounding tissue as a result of capacitive coupling is inhibited.

At the completion of tissue treatment, e.g., dissection, monopolar assembly 200 may be returned to the retracted position (FIGS. 4A-4B), e.g., via translating slide knob 64 of slide assembly 60 proximally along slot 22 to proximal end 23 thereof. With monopolar assembly 200 once again in the retracted position, jaw members 110, 120 of end effector assembly 100 may be manipulated to grasp, treat, and/or cut tissue, as described above, in the bipolar mode.

Turning now to FIGS. 5 and 5A-5D, monopolar assembly 200 is shown including a plurality of distal tips 224a, 224b, 224c, 224d configured for use therewith. As mentioned above, distal tips 224a, 224b, 224c, 224d may be releasably engagable with body 222 of inner tubular member 220 of monopolar assembly 200. More specifically, body 222 of inner tubular member 220 includes an engagement feature, e.g., threading 226, defined at distal end 223 thereof, while distal tips 224a, 224b, 224c, 224d each include a complementary engagement feature, e.g., complementary threading 228, at the proximal end thereof for releasable engagement with threading 226 of body 222 of inner tubular member 220. Other releasably engagement features are also contemplated, e.g., friction-fitting, latching, etc.

With continued reference to FIGS. 5 and 5A-5D, various different configurations of distal tips 224a, 224b, 224c and 224d are shown. Distal tip 224a is shown including a beveled distal end 225a; distal tip 224b is shown including a generally linear blade 225b extending distally therefrom; distal tip 224c is shown including a hook 225c extending distally therefrom; and distal tip 224d is shown defining a generally annular distal end 225d. Other configurations may also be provided. A desired configuration of distal tip may be selected and engaged to body 222 of inner tubular member 220 depending on the particular purpose. For example, where it is desired to treat tissue via distal advancement of forceps 10 (FIG. 1), distal tip 224a, distal tip 224b, or distal tip 224d may be selected (depending on the size and/or composition of tissue to be dissected). On the other hand, where it is desired to treat tissue via proximal movement of forceps 10 (FIG. 1), distal tip 224c may be selected.

Various other embodiments of end effector assemblies and/or monopolar assemblies provided in accordance with the present disclosure and configured for use with forceps 10 (FIG. 1) or any other suitable surgical instrument are described below with reference to FIGS. 6A-10. These end effector assemblies and/or monopolar assemblies are similar to end effector assembly 100 and monopolar assembly 200 (see FIGS. 1-3), respectively, described above. Accordingly, for purposes of brevity, only the differences will be described hereinbelow, keeping in mind that any or all of the features of end effector assembly 100 (FIG. 2), monopolar assembly 200 (FIG. 3), and/or forceps 10 (FIG. 1), to the extent consistent, may similarly apply to the end effector assemblies, monopolar assemblies, and instruments associated therewith, respectively, described below.

Figure 6A:
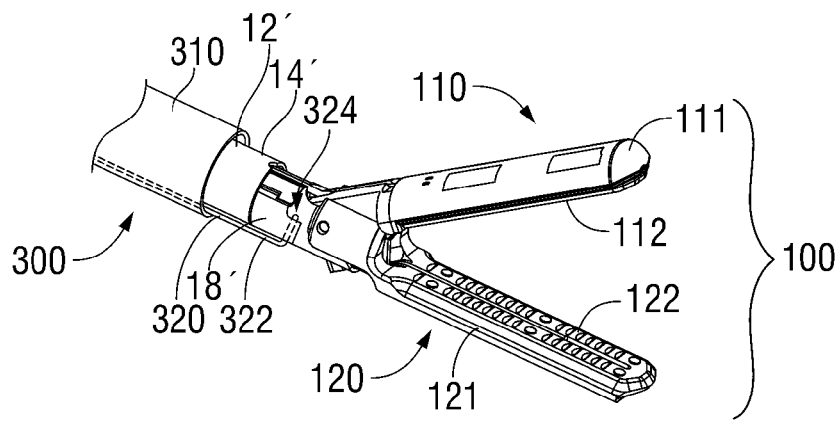
FIG. 6A is a side, perspective view of another end effector assembly configured for use with the forceps of FIG. 1 including a monopolar assembly disposed in a retracted position.
Figure 6B:
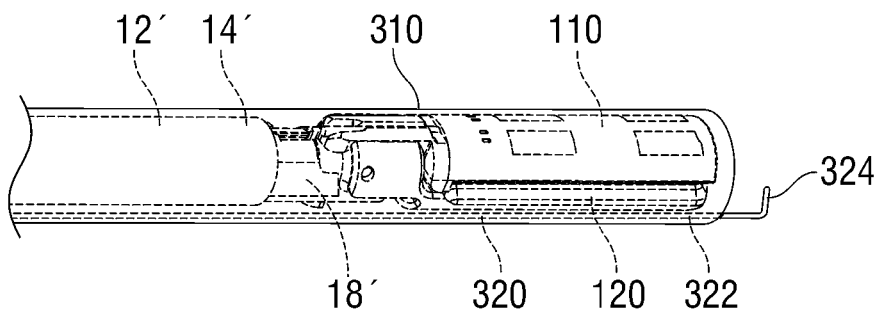
FIG. 6B is a side, perspective view of the end effector assembly of FIG. 6A with the monopolar assembly disposed in an extended position.

Turning now to FIGS. 6A-6B, another embodiment of a monopolar assembly provided in accordance with the present disclosure is shown generally identified by reference numeral 300. Monopolar assembly 300 is configured for use with end effector assembly 100 and a forceps similar to forceps 10 (FIG. 1), except that shaft 12' of the forceps further includes an insulative member, e.g., distal sleeve 18', mounted thereon towards distal end 14' thereof that is configured to receive electrically-conductive monopolar rod member 320 therein when monopolar assembly 300 is disposed in the retracted position, as will be described below. Further, monopolar assembly 300 is similar to monopolar assembly 200 (FIG. 3), except that, rather than including an electrically-conductive inner tubular member 220 (FIG. 3), monopolar assembly 300 includes a monopolar rod member 320 having an exposed electrically-conductive portion, e.g., distal tip 324.

With continued reference to FIGS. 6A-6B, monopolar assembly 300 includes an electrically-insulative outer tubular member 310 that is disposed about shaft 12' and a monopolar rod member 320 that extends through outer tubular member 310 (adjacent shaft 12') and distally therefrom, ultimately defining an exposed electrically-conductive hook-shaped distal tip 324 (although other configurations may also be provided). Rod member 320 and, more specifically, distal tip 324 thereof, functions as the active electrode of monopolar assembly 300. Outer tubular member 310 may be fixedly engaged to rod member 320 such that outer tubular member 310 and rod member 320 move in concert with one another between the retracted position (FIG. 6A) and the extended position (FIG. 6B), e.g., upon translation of slide knob 64 (FIG. 1). Alternatively, outer tubular member 310 and rod member 320 may be coupled to one another to effect simultaneous but differential deployment of outer tubular member 310 and rod member 320 relative to one another, or may be independent of one another such that outer tubular member 310 and/or rod member 320 may be selectively deployed independently of one another.

In the retracted position, as shown in FIG. 6A, distal tip 324 of monopolar assembly 300 is disposed within an insulating member, e.g., distal sleeve 18' of shaft 12', disposed towards distal end 14' of shaft 12'. Distal sleeve 18' is electrically-insulated such that distal tip 324 of rod member 320 is isolated from tissue sealing plates 112, 122 of jaw members 110, 120, respectively, and from surrounding tissue when disposed in the retracted position, thereby inhibiting capacitive coupling and resulting damage to surrounding tissue.

In the extended position, as shown in FIG. 6B, outer tubular member 310 is disposed about jaw members 110, 120 of end effector assembly 100, while distal tip 324 of rod member 320 extends distally therefrom. In this position, energy may be applied to distal tip 324 of rod member 320 to treat tissue. A return pad (not shown) positioned at a remote location is used to return energy transmitted from distal tip 324 of rod member 320 through tissue. Further, in the extended position, monopolar assembly 300 and, more particularly, rod member 320 thereof, may be rotated relative to end effector assembly 100, e.g., via rotating a second rotating assembly (similar to rotating assembly 70 (FIG. 1)) disposed within housing 20 (FIG. 1) and coupled to monopolar assembly 300, to better position distal tip 324 of rod member 320 relative to tissue.

Figure 6C:
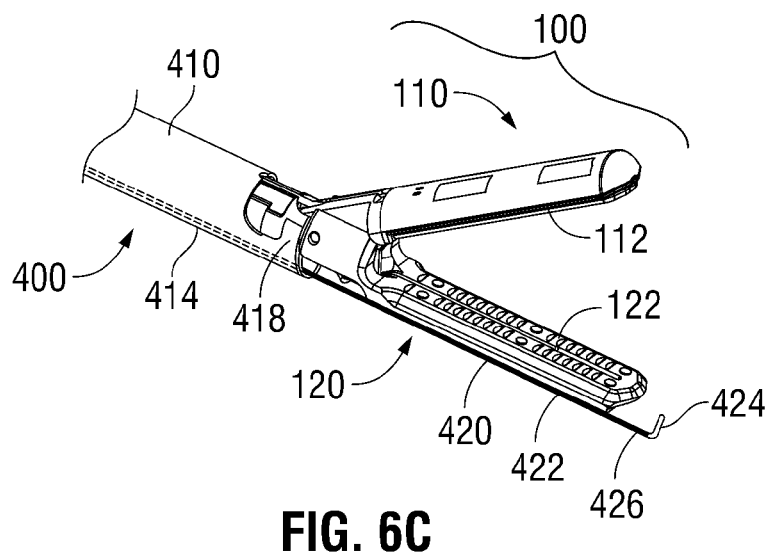
FIG. 6C is side, perspective view of another end effector assembly configured for use with the forceps of FIG. 1 including a monopolar assembly disposed in an extended position.

Turning to FIG. 6C, another embodiment of a monopolar assembly 400 similar to monopolar assembly 300 is shown. Monopolar assembly 400 differs from monopolar assembly 300 in that insulative outer tubular member 410 of monopolar assembly 400 forms the shaft of the forceps (or is fixedly disposed about the shaft of the forceps) and is fixed in position relative to end effector assembly 100. Monopolar rod member 420 extends through and distally from outer tubular member 410 and is movable relative to end effector assembly 100 and insulative outer tubular member 410 between the retracted position and the extended position. Rod member 420 may include an insulative sleeve or coating 426 disposed about body portion 422 thereof, such that distal hook 424 is the only exposed electrically-conductive portion of rod member 420. Distal hook 424 of rod member 420 is received within a recess defined within a distal sleeve 418 that extends from distal end 414 of outer tubular member 410 when in the retracted position, thereby helping to protect surrounding tissue.

Figure 6D:
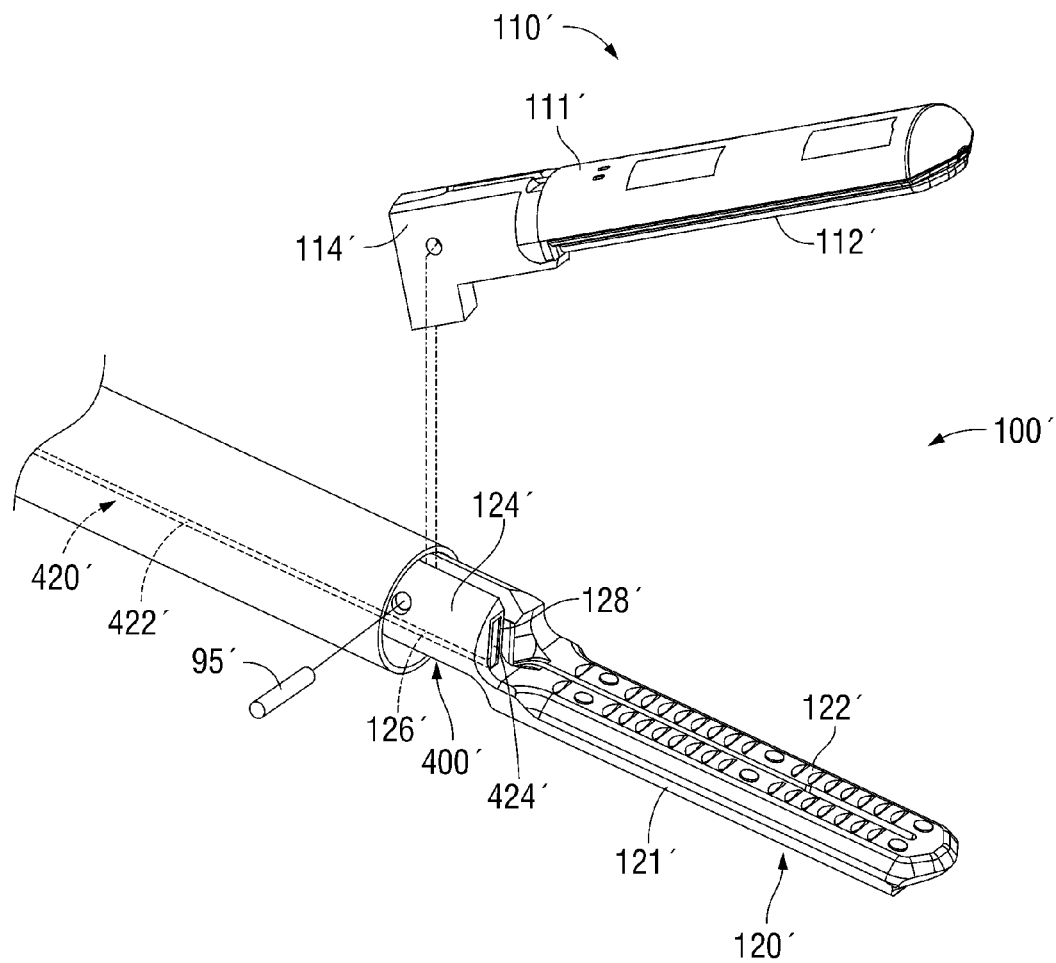
FIG. 6D is side, perspective view of another end effector assembly configured for use with the forceps of FIG. 1 and shown with parts separated, the end effector assembly including a monopolar assembly disposed in a retracted position.

Referring to FIG. 6D, another embodiment of an end effector assembly 100' incorporating a monopolar assembly 400' is shown. End effector assembly 100' is similar to end effector assembly 100 (FIGS. 1-4D), while monopolar assembly 400' is similar to monopolar assembly 300 (FIGS. 6A-6B) and monopolar assembly 400 (FIG. 6C). Accordingly, only the differences between end effector assembly 100' and monopolar assembly 400' as compared to the previous embodiments described hereinabove will be described in detail below.

Continuing with reference to FIG. 6D, each jaw member 110', 120' of end effector assembly 100' includes a distal jaw portion 111', 121' including a tissue sealing surface defined by an electrically-conductive tissue-sealing plate 112', 122', and a proximal flange 114', 124' extending proximally from the respective distal jaw portion 111', 121'. Proximal flanges 114', 124' are configured to receive pivot pin 95' to pivotably couple jaw members 110', 120' to one another and may be formed at least partially from, or coated at least partially with an insulative material. The proximal flange of one of the jaw members, e.g., proximal flange 124' of jaw member 120', further defines a lumen 126' extending therethrough and a recess 128' defined within the distal surface of proximal flange 124' that communicates with lumen 126'. This configuration of proximal flange 124' of jaw member 120' permits body 422' of rod member 420' of monopolar assembly 400' to extend through proximal flange 124' of jaw member 120', e.g., through lumen 126', while also permitting distal hook 424' of rod member 420' of monopolar assembly 400' to be received within recess 128' of proximal flange 124' when monopolar assembly 400' is disposed in the retracted position, thereby helping to protect surrounding tissue. In other words, rather than providing an insulative sleeve for retaining monopolar assembly 400' when monopolar assembly 400' is disposed in the retracted position, jaw member 120' itself is configured to retain monopolar assembly 400' therein when monopolar assembly 400' is disposed in the retracted position.

Figure 6E:
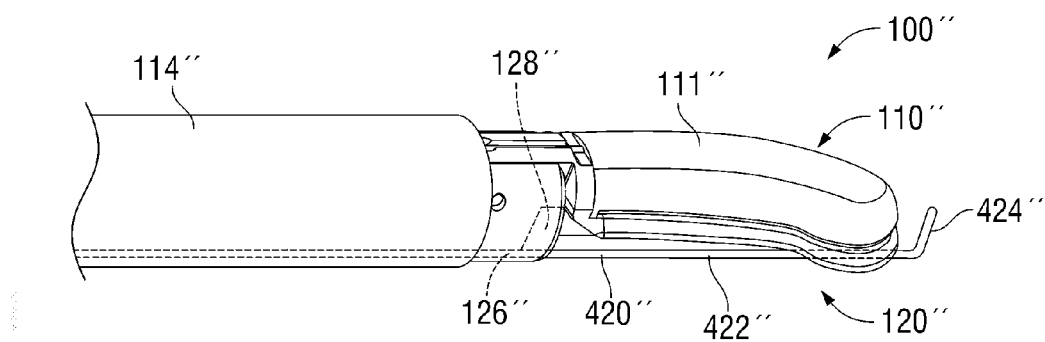
FIG. 6E is a top, perspective view of another end effector assembly configured for use with the forceps of FIG. 1 shown including a monopolar assembly disposed in an extended position.
Figure 6F:
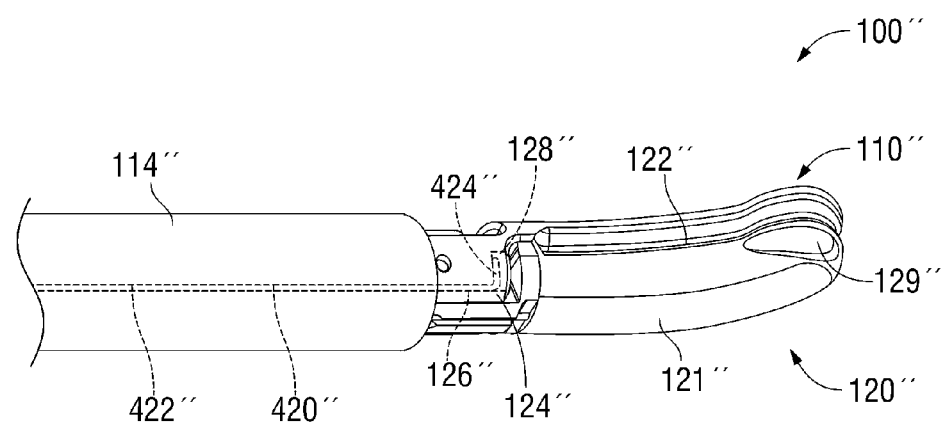
FIG. 6F is a bottom, perspective view of the end effector assembly of FIG. 6E shown including the monopolar assembly disposed in a retracted position.

Turning now to FIGS. 6E-6F, another embodiment of an end effector assembly 100" incorporating a monopolar assembly 400" is shown. End effector assembly 100" is similar to end effector assembly 100' (FIG. 6D), while monopolar assembly 400" is similar to monopolar assembly 400' (FIG. 6D), although end effector assembly 100" and/or monopolar assembly 400" may alternatively be configured similarly to any of the other end effector assemblies and monopolar assemblies described herein. For purposes of brevity, only the differences between end effector assembly 100" and monopolar assembly 400" as compared to end effector assembly 100' (FIG. 6D) and monopolar assembly 400' (FIG. 6D), respectively, will be described in detail below.

With continued reference to FIGS. 6E-6F, each jaw member 110", 120" of end effector assembly 100" includes a distal jaw portion 111", 121" having a tissue-sealing plate 112", 122" disposed thereon, and a proximal flange 114", 124" extending proximally from the respective distal jaw portion 111", 121". The proximal flange of one of the jaw members, e.g., proximal flange 124" of jaw member 120", further defines a lumen 126" and a recess 128" configured to receive body 422" of rod member 420" of monopolar assembly 400" and distal hook 424" of rod member 420" of monopolar assembly 400", respectively, when monopolar assembly 400" is disposed in the retracted position (FIG. 6F). Further, jaw members 110" and 120" of end effector assembly 100" define curved configurations, e.g., to facilitate manipulation of tissue and to provide better "line of sight" for accessing targeted tissues, although other configurations may also be provided. More specifically, jaw members 110", 120" are curved towards the side of end effector assembly 100" wherein monopolar assembly 400" is disposed, such that the overall width dimension of end effector assembly 100" is not increased by the presence of monopolar assembly 400".

One of the jaw members, e.g., jaw member 120", includes a channel-shaped cut-out 129" defined within distal jaw portion 121" towards the distal end thereof. Cut-out 129" is configured to permit reciprocation of monopolar assembly 400" between the retracted position, wherein monopolar assembly 400" is disposed within proximal flange 124" of jaw member 120", and the extended position, wherein distal hook 424" of monopolar assembly 400" extends distally from end effector assembly 100". More specifically, due to the curved configurations of jaw members 110", 120", the distal end of jaw member 120" curves into the path of monopolar assembly 400". Cut-out 129" defines a channel through which monopolar assembly 400" is configured to extend, thus permitting extension of distal hook 424" distally beyond end effector assembly 100" without interference by jaw member 120" and guiding the extension/retraction of monopolar assembly 400".

With reference to FIGS. 7A-7B, a jaw member 520 of an end effector assembly 500 that incorporates a monopolar rod member 530 therein is shown. Jaw member 520, similar to jaw members 110, 120 of end effector assembly 100 (see FIGS. 1-3), includes an insulative outer jaw housing 521 and an electrically-conductive tissue sealing plate 522 disposed atop jaw housing 521. However, jaw housing 521 further includes a lumen (not explicitly shown) extending therethrough that is configured to slidably receive body 532 of rod member 530 and a complementary-shaped recess 528 defined therein that communicates with the lumen (not explicitly shown). Recess 528 is defined within distal end 523 of jaw member 520 and is configured to receive distal tip 534 of rod member 530 therein when rod member 530 is disposed in the retracted position. More specifically, in the retracted position, rod member 530 is fully disposed within recess 528 of jaw housing 521 of jaw member 520 such that rod member 530 is electrically insulated from tissue sealing plate 522 (and the tissue sealing plate of the other jaw member (not shown) of end effector assembly 500). In the extended position, rod member 530 extends distally from recess 528 and jaw member 520 to facilitate monopolar tissue treatment. As in the previous embodiments, an insulative tubular member (not explicitly shown) may be provided to slide distally over and further electrically insulate end effector assembly 500 from rod member 530 as rod member 530 is moved to the extended position. Rod member 530 may also be rotatable relative to end effector assembly 500.

Referring to FIGS. 8A-8B, another embodiment of an end effector assembly 600 similar to end effector assembly 500 (FIGS. 7A-7B) is shown including a monopolar wire member 630 within one of the jaw members 610, 620, e.g., jaw member 620. More specifically, jaw member 620 includes a lumen 626 extending longitudinally through insulative jaw housing 621 thereof and an electrically-conductive monopolar wire member 630 slidably received within lumen 626. At least a portion of wire member 630 is formed from a resilient material, or is otherwise configured such that distal tip 634 of wire member 630 is capable of assuming a substantially linear configuration relative to body 632 of wire member 630, thus permitting wire member 630 to be completely retracted within lumen 626 in a substantially linear configuration. Upon extension of wire member 630 from lumen 626, e.g., upon movement of wire member 630 to the extended position, distal tip 634 of wire member 630 assumes a curved, hook-shaped, or other suitable configuration to facilitate tissue dissection. Wire member 630 may also be rotatable relative to jaw member 620 when in the extended position, similarly as described above with respect to rod member 330 (FIGS. 6A-6B). Further, an outer insulative sleeve (not shown) may also be provided to surround end effector assembly 600 upon extension of monopolar member 630, similarly as described above with respect to the previous embodiments.

Figure 9A:
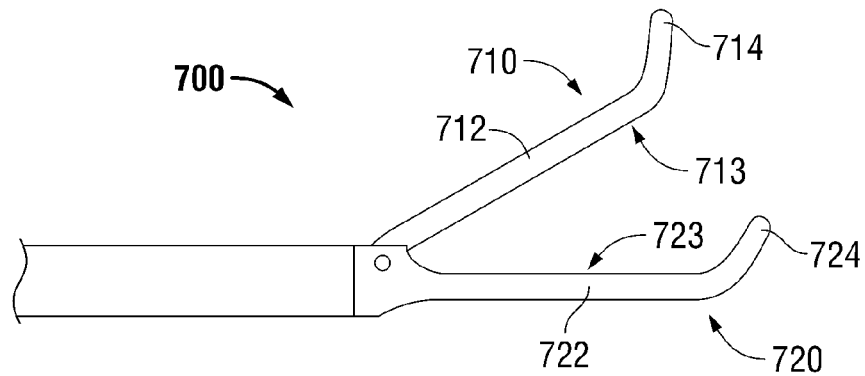
FIG. 9A is a side view of another end effector assembly configured for use with the forceps of FIG. 1 with jaw members disposed in a spaced-apart position.
Figure 9B:
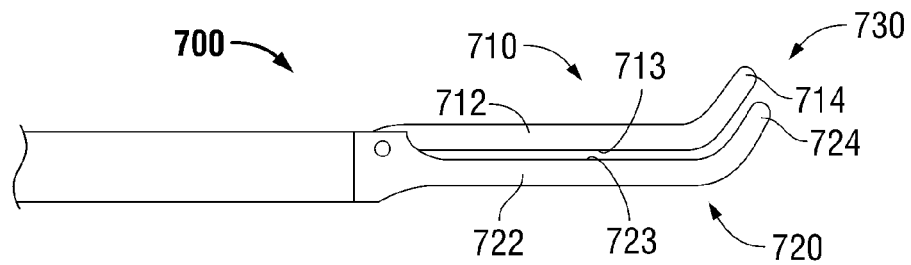
FIG. 9B is a side view of the end effector assembly of FIG. 9A with the jaw members disposed in an approximated position.

Turning now to FIGS. 9A-9B, another embodiment of an end effector assembly provided in accordance with the present disclosure is shown generally indentified by reference numeral 700. End effector assembly 700 includes first and second electrically-conductive jaw members 710, 720 (although a portion of jaw members 710, 720 may be covered with or coated by an insulative material) that are movable relative to one another between a spaced-apart position and an approximated position for grasping tissue therebetween. Each jaw member 710, 720 includes a generally linear body portion 712, 722 defining a tissue sealing surface 713, 723, respectively. One or both of the jaw members 710, 720 further includes a hook-shaped, or curved distal portion 714, 724, respectively, extending from respective body portion 712, 722 thereof. Jaw members 710, 720 are adapted to connect to a source of energy (not explicitly shown) for supplying energy thereto in each of a bipolar mode and a monopolar mode. More specifically, in the bipolar mode, jaw member 710 is charged to a first electrical potential and jaw member 720 is charged to a second, different electrical potential such that an electrical potential gradient is created for conducting energy therebetween and through tissue grasped therebetween for treating e.g., sealing, tissue.

In the monopolar mode, on the other hand, jaw members 710, 720 are approximated and energized to the same electrical potential such that energy is conducted from jaw members 710, 720 and, more particularly, distal portions 714, 724, respectively, thereof, through tissue to a remotely located return pad (not explicitly shown) for treating, e.g., dissecting, tissue. The particular configuration of jaw members 710, 720, e.g., wherein either or both jaw members 710, 720 include hooked distal portions 714, 724, respectively, facilitates monopolar dissection of tissue in that, when jaw members 710, 720 are disposed in the approximated position, hooked distal portion 714 and/or hooked distal portion 724 (either alone or in cooperation with one another) define a monopolar, active electrode probe 730. That is, rather than providing a separate monopolar element, distal portions 714, 724 of jaw members 710, 720, respectively, function as the monopolar element when operating in the monopolar mode.

Figure 9C:
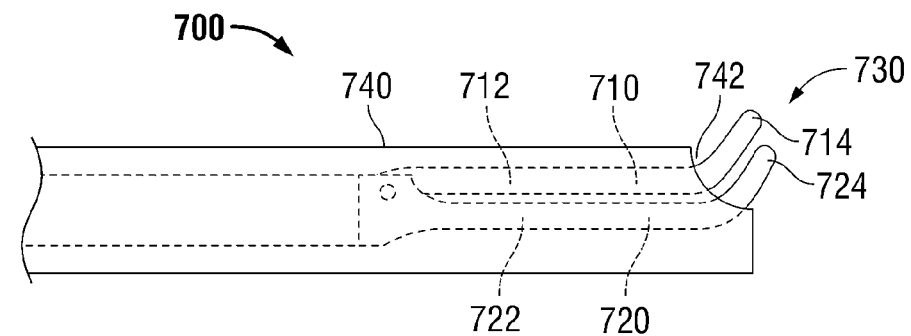
FIG. 9C is a side view of the end effector assembly of FIG. 9A with the jaw members disposed in the approximated position and including an insulative sleeve disposed thereabout.

Turning to FIG. 9C, end effector assembly 700, in some embodiments, may further include an insulative tubular member 740 disposed about body portions 712, 722 of jaw members 710, 720, respectively. Insulative tubular member 740 includes a distal cut-out 742 such that monopolar probe 730, e.g., hooked distal portions 714, 724 of jaw member 710, 720, is exposed when insulative tubular member 740 is extended about end effector 700 to facilitate monopolar tissue treatment. This configuration also protects surrounding tissue by electrically isolating body portions 712, 722 of jaw members 710, 720, respectively, from surrounding tissue during operation in the monopolar mode. Insulative tubular member 740 may be extended and retracted similarly as described above with respect to any of the previous embodiments.

Figure 10:
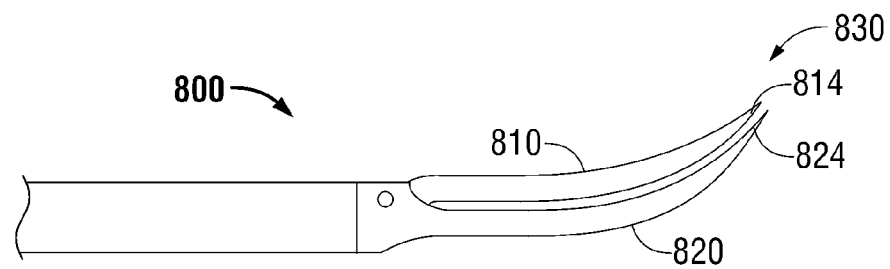
FIG. 10 is a side view of another end effector assembly configured for use with the forceps of FIG. 1.

With reference to FIG. 10, another embodiment of an end effector assembly provided in accordance with the present disclosure and configured for operation in both a bipolar mode and a monopolar mode is shown generally indentified by reference numeral 800. End effector assembly 800 is similar to end effector assembly 700 (FIGS. 9A-9C), except that, rather than including generally linear body portions and hook-shaped distal portions, jaw members 810, 820 define complementary curved configurations substantially along the lengths thereof. The curved configurations of jaw members 810, 820 facilitate spreading and/or separating tissue to provide access to underlying tissue for grasping, treating, e.g., sealing, and/or dividing the underlying tissue (in the bipolar mode). Further, similar to end effector assembly 700 (FIGS. 9A-9C), a monopolar, active electrode probe 830 is formed via the cooperation of distal ends 814, 824 of jaw members 810, 820, respectively, when jaw members 810, 820 are disposed in the approximated position, thereby facilitating monopolar tissue treatment (in the monopolar mode). Any of the other features of end effector assembly 700 (FIGS. 9A-9C), described above and to the extent consistent, apply similarly to end effector assembly 800 and, thus, are not repeated here.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a housing;
    a shaft extending distally from the housing;
    an end effector assembly disposed at a distal end of the shaft; and
    a monopolar assembly including a tubular member and a monopolar electrode, the tubular member at least partially formed from an insulative material and slidably disposed about the shaft, the monopolar electrode engaged to the tubular member, disposed at least partially within the tubular member, and extending distally from the tubular member,
    wherein the monopolar assembly is deployable from a retracted position, wherein the tubular member is positioned proximally of the end effector assembly and a distal end of the monopolar electrode is positioned towards a proximal end of the end effector assembly, and an extended position, wherein the tubular member surrounds the end effector assembly and the distal end of the monopolar electrode extends distally from the end effector assembly.

2. The surgical instrument according to claim 1, wherein the end effector assembly includes first and second jaw members pivotably coupled to one another, at least one of the first or second jaw members pivotable relative to the other between a spaced-apart position and an approximated position.

3. The surgical instrument according to claim 2, wherein each of the first and second jaw members includes an electrically-conductive surface, the electrically-conductive surfaces configured to conduct bipolar energy therebetween.

4. The surgical instrument according to claim 2, further comprising:
    a movable handle operably coupled to the housing; and
    a drive assembly coupled between the movable handle and the at least one of the first or second jaw members,
    wherein actuation of the movable handle pivots the at least one of the first or second jaw members relative to the other from the spaced-apart position to the approximated position.

5. The surgical instrument according to claim 2, wherein each of the first and second jaw members includes a proximal flange and a distal jaw body, and wherein, in the retracted position of the monopolar assembly, the distal end of the monopolar electrode is positioned adjacent the proximal flange of at least one of the first or second jaw members.

6. The surgical instrument according to claim 1, further comprising an actuation knob operably coupled to the housing and the monopolar assembly, wherein actuation of the actuation knob deploys the monopolar assembly from the retracted position to the extended position.

7. The surgical instrument according to claim 1, wherein the monopolar electrode includes an elongated proximal portion and a distal tip portion.

8. The surgical instrument according to claim 7, further comprising and insulator disposed about at least a portion of the elongated proximal portion of the monopolar electrode.

9. The surgical instrument according to claim 7, wherein the distal tip portion of the monopolar electrode defines a hook-shaped configuration.

10. The surgical instrument according to claim 1, further comprising a monopolar activation switch disposed on the housing and electrically coupled to monopolar electrode.

11. The surgical instrument according to claim 1, wherein, in the extended position, a distal end of the tubular member is positioned adjacent a distal end of the end effector assembly.

12. A surgical instrument, comprising:
    a housing;
    a shaft extending distally from the housing;
    an end effector assembly disposed at a distal end of the shaft, the end effector assembly including first and second jaw members pivotably coupled to one another, at least one of the first or second jaw members pivotable relative to the other between a spaced-apart position and an approximated position, each of the first and second jaw members including an electrically-conductive surface adapted to connect to a source of bipolar energy; and
    a monopolar assembly including a tubular member and a monopolar electrode, the tubular member at least partially formed from an insulative material and slidably disposed about the shaft, the monopolar electrode engaged to the tubular member, disposed at least partially within the tubular member, and extending distally from the tubular member, the monopolar electrode adapted to connect to a source of monopolar energy,
    wherein the monopolar assembly is deployable from a retracted position, wherein the tubular member is positioned proximally of the end effector assembly and a distal end of the monopolar electrode is positioned towards a proximal end of the end effector assembly, and an extended position, wherein the tubular member surrounds the end effector assembly and the distal end of the monopolar electrode extends distally from the end effector assembly.

13. The surgical instrument according to claim 11, further comprising:
    a movable handle operably coupled to the housing; and
    a drive assembly coupled between the movable handle and the at least one of the first or second jaw members,
    wherein actuation of the movable handle pivots the at least one of the first or second jaw members relative to the other from the spaced-apart position to the approximated position.

14. The surgical instrument according to claim 11, wherein each of the first and second jaw members includes a proximal flange and a distal jaw body, and wherein, in the retracted position of the monopolar assembly, the distal end of the monopolar electrode is positioned adjacent the proximal flange of at least one of the first or second jaw members.

15. The surgical instrument according to claim 11, further comprising an actuation knob operably coupled to the housing and the monopolar assembly, wherein actuation of the actuation knob deploys the monopolar assembly from the retracted position to the extended position.

16. The surgical instrument according to claim 11, wherein the monopolar electrode includes an elongated proximal portion and a distal tip portion.

17. The surgical instrument according to claim 15, further comprising and insulator disposed about at least a portion of the elongated proximal portion of the monopolar electrode.

18. The surgical instrument according to claim 15, wherein the distal tip portion of the monopolar electrode defines a hook-shaped configuration.

19. The surgical instrument according to claim 11, further comprising a monopolar activation switch disposed on the housing and electrically coupled to monopolar electrode.

20. The surgical instrument according to claim 11, further comprising a bipolar activation switch disposed on the housing and electrically coupled to at least one of the electrically-conductive surfaces of the first and second jaw members.

* * * * *